(12) United States Patent
Arbel

(10) Patent No.: US 6,496,739 B2
(45) Date of Patent: Dec. 17, 2002

(54) ELECTRODE POSITIONER FOR A SPLINT TO BE USED FOR MUSCLE STIMULATION

(75) Inventor: Glora Arbel, Kfar-Saba (IL)

(73) Assignee: N.E.S.S. Neuromuscular Electrical Stimulation Systems Ltd., Ra'anana (IL)

(*) Notice: Subject to any disclaimer, the term of this patent is extended or adjusted under 35 U.S.C. 154(b) by 76 days.

(21) Appl. No.: 09/832,110

(22) Filed: Apr. 11, 2001

(65) Prior Publication Data

US 2002/0032475 A1 Mar. 14, 2002

(30) Foreign Application Priority Data

Apr. 11, 2000 (IL) .................................................. 135585

(51) Int. Cl.[7] ................................................ A61N 1/04
(52) U.S. Cl. ...................................................... 607/149
(58) Field of Search ............................... 607/46, 48–50, 607/115, 144, 149

(56) References Cited

U.S. PATENT DOCUMENTS

| 5,330,516 A | 7/1994 | Nathan | 607/48 |
| 5,540,735 A | 7/1996 | Wingrove | 607/46 |
| 5,766,236 A * | 6/1998 | Detty et al. | 607/149 |

FOREIGN PATENT DOCUMENTS

| WO | WO95/10323 | 4/1995 |
| WO | WO98/53877 | 12/1998 |

* cited by examiner

Primary Examiner—George R. Evanisko
(74) Attorney, Agent, or Firm—Jacobson Holman PLLC

(57) ABSTRACT

The invention provides a set of electrode positioners for skin-contacting surface electrodes used for electrical muscular stimulation in conjunction with a splint, the set including at least one electrode positioner in the form of a scoop-like structure, the concave surface of which substantially fits a first surface of a patient's limb; at least one surface electrode of a predetermined size, location and orientation, fixedly attached to the concave surface, and a terminal element for connecting the at least one electrode to a source of stimulation current, the terminal element being accessible from the rear side of the concave surface, wherein the electrode positioner is configured to be introductive between the surface of the limb and an interior surface of the splint, an element is also provided to arrest the positioner in a predetermined and reproducible final position relative to the splint.

9 Claims, 3 Drawing Sheets

Fig.1.
Fig.2.
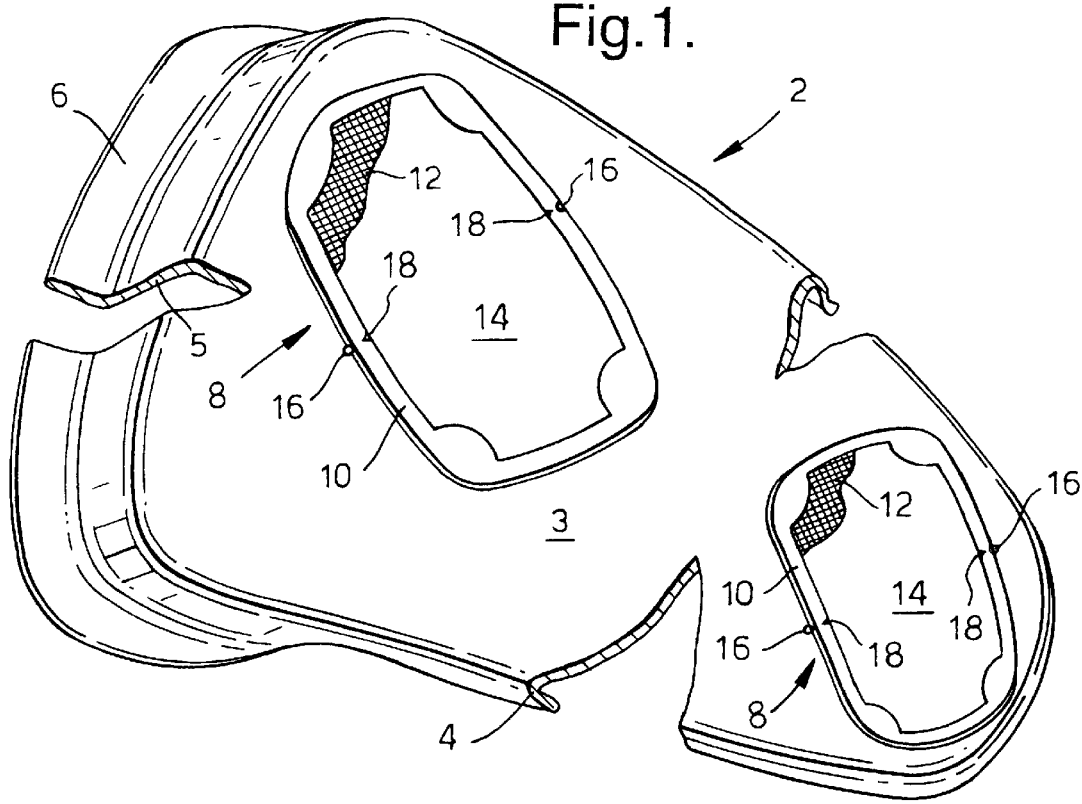
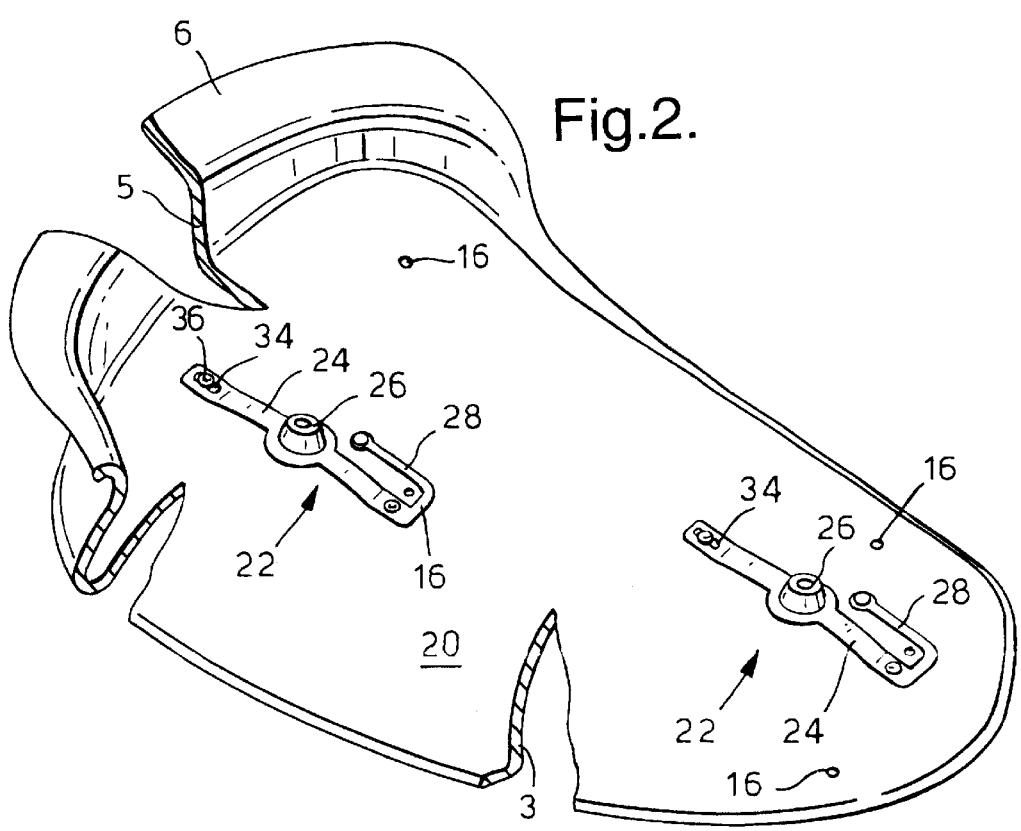

ELECTRODE POSITIONER FOR A SPLINT TO BE USED FOR MUSCLE STIMULATION

FIELD OF THE INVENTION

The present invention relates to a set of electrode positioners, in particular to electrode positioners for skin-contacting surface electrodes used for electrical muscular stimulation in conjunction with a splint.

BACKGROUND OF THE INVENTION

Electrical stimulation is widely used for pain control (TENS), therapeutic exercise (TESS) and for activating a paralyzed limb (FEES) in order to restore functional activities, e.g., pretension-release of objects. A serious problem encountered by a patient is the need to position the electrodes on his limb each time he sets up the stimulation system. Electrode positioning requires considerable expertise and a great deal of time, especially when the stimulation system is required to activate several muscles in relatively complex movements, and even more so when the muscles are small and the musculature is crowded. For limbs such as the forearm, it is very difficult to position an array of surface electrodes sufficiently accurately to generate a prehension-release pattern in the hand which would facilitate grasp and manipulation of objects and utensils in daily use.

One solution to the above problem has been to arrange the electrodes on the inside surface of a splint, as shown, by way of example, in FIG. 1 of U.S. Pat. No. 5,330,516. During an initial clinical session with the patient, the clinician applies his expertise and arranges the electrode array on the splint. Thereafter, every time the patient uses the device, he places the splint on his arm and the entire electron array locates itself according to the clinician's arrangement. The problem of this method resides in the fact that even for an experienced clinician, the positioning of electrodes for optimum results is a very time-consuming process, which is also correspondingly wearisome to the patient.

DISCLOSURE OF THE INVENTION

It is thus one of the objects of the present invention to provide a set of electrode positioners that enables a clinician to assess the efficiency of a diversity of electrode locations on the limb of a patient in rapid succession and that, after he has rapidly gone through and tested several or all of the electrode positioners of the set, allows him to attach permanent surface electrodes to the splint, the size, position and orientation of the, electrodes being precisely copied from those of the selected electrode positioners.

It is a further object of the present invention to provide an electrode positioner that will enable the patient himself to activate different muscles of his limb to carry out a variety of functional activities, as well as to exercise his limb using a selection of clinical protocols, choosing different muscles each time.

According to the invention, the above objects are achieved by providing a set of electrode positioners for skin-contacting surface electrodes used for electrical muscular stimulation in conjunction with a splint, said set comprising at least one electrode positioner in the form of a scoop-like structure, the concave surface of which substantially fits a first surface of a patient's limb; at least one surface electrode of a predetermined size, location and orientation, fixedly attached to said concave surface; terminal means for connecting said at least one electrode to a source of stimulation current, said terminal means being accessible from the rear side of said concave surface, wherein said electrode positioner is configured to be introducible between the surface of said limb and an interior surface of said splint, means being provided to arrest said positioner in a predetermined and reproducible final position relative to said splint.

It will be appreciated that the electrode positioners described below are designed for use with splints intended for the activation, by electrical stimulation, of flexor and extensor muscles, the motor points of which are located in the palmar, respectively, the dorsal, portions of the forearm. Since any useful limb movement requires the action of a flexor as well as an extensor, it is obvious that such a splint must have stimulation electrodes on both the dorsal and palmar sides of the forearm and therefore requires at least two electrode positioners.

It will be further appreciated that a forearm splint was selected by way of example only, splints being feasible also for the lower limbs, the elbow, the shoulder, etc. In such cases, while the mounting and operating principles of the associated electrode positioners remain the same, their specific shape will obviously be dictated by their points of application.

BRIEF DESCRIPTION OF THE DRAWINGS

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a perspective view, electrode side up, of an electrode positioner for the dorsal side of a splint;

FIG. 2 is a perspective view of the rear side of the electrode positioner of FIG. 1;

FIG. 3 is a side view of a terminal element of the electrode positioner;

FIG. 4 represents a perspective view, electrode side up, of an electrode positioner for the palmar side of a splint;

FIG. 5 is a perspective view of the rear side of the electrode positioner of FIG. 4, and FIG. 6 is a perspective view of a patient's arm wearing a splint, with the positioner of FIG. 1 being introduced between the dorsal portion of the splint and the patient's skin.

DETAILED DESCRIPTION

Figure 3:
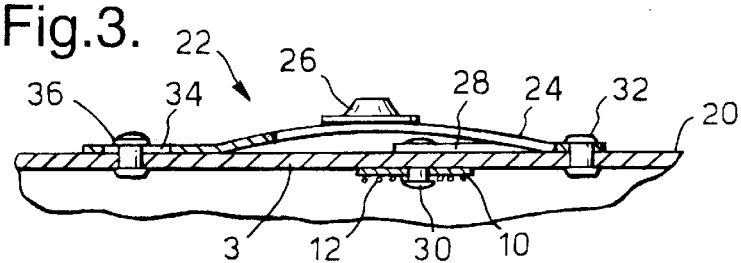

Referring now to the drawings, there is shown in FIG. 1 an electrode positioner designed for the dorsal part of a forearm, comprising a scoop-like structure 2 advantageously produced from plastic sheeting by vacuum-forming and provided with beaded rims 4 which, at the wider end of structure 2, turn into a heel 5 and a flange 6, which latter is used to facilitate handling of structure 2.

Also shown are two surface electrodes 8, comprised of an electrode carrier 10 attached to the concave surface 3 of structure 2 with the aid of a double-faced adhesive patch (not shown), the electrode proper 12 in the form of a fine wire mesh fixedly attached to electrode carrier 10, and a skin-contacting pad 14. A detailed description of surface electrode 8 can be found in co-pending Israel Patent Application No. 135,175. Surface electrodes 8 activate extensor muscles.

Further seen in FIG. 1 are two small holes 16 on the rim of each electrode carrier 10, so disposed that their respective centers are located on the edges of the rims, each hole 16 being located directly opposite index markings 18 provided on the rims. The purpose of these holes will become apparent further below.

FIG. 2 shows the rear side of structure 2, the surface 20 of which is obviously convex. Seen are two terminal elements 22, one for each of surface electrodes 8 (FIG. 1). An enlarged side view of element 22 is shown in FIG. 3. There is seen a flat spring 24 prebent to a flat, arch-like shape and carrying a tapered projection 26. At one of its ends, spring 24 is provided with a tongue-like appendage 28 which, by means of an advantageously hollow rivet 30, electrically connects terminal element 22 with electrode 12 (pad 14 not shown). At one end, spring 24 is fixedly attached to structure 2 by means of a rivet 32. The other end of spring 24 is provided with an elongated hole 34 and is held down by a washer 36 that permits spring 24 to stretch when it is flattened by pressure on projection 26. The purpose of this arrangement will be explained further below.

Figure 4:
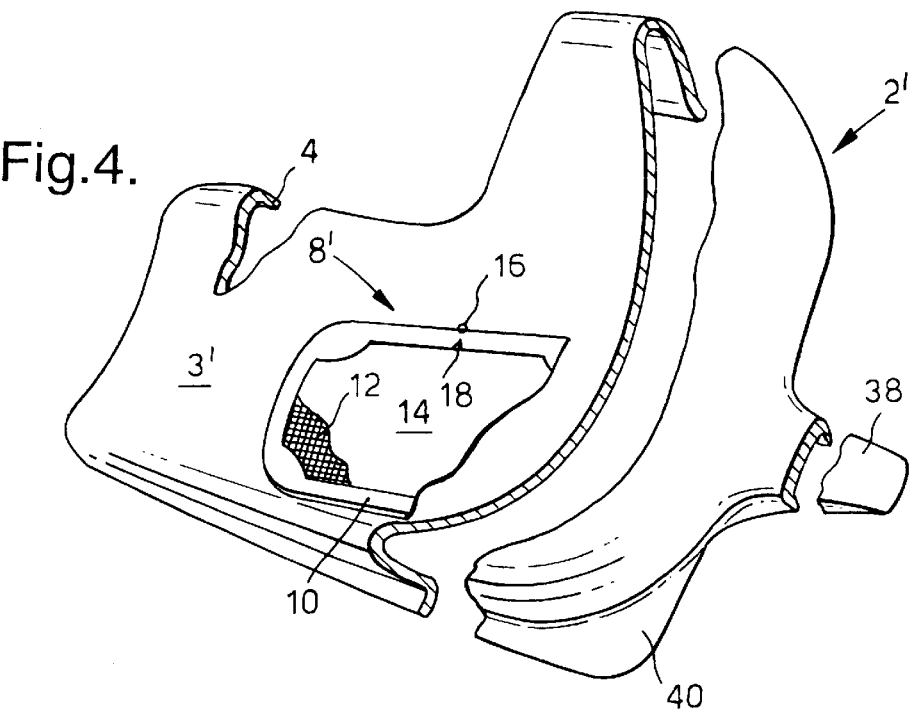

FIG. 4 illustrates the counterpart of the electrode positioner shown in FIG. 1, namely, the electrode positioner designed for the palmar portion of the forearm. Seen is scoop-like structure 2', which is of a slightly different configuration, designed as it is for the palmar section of the splint. Beaded rims 4, at the wide end of structure 2', turn into a cable duct 38 and an ear-like grip 40 for handling structure 2'. The single surface electrode 8', mounted on concave surface 3', is meant to activate flexor muscles and consists of the same components as surface electrodes 8 seen in FIG. 1.

Figure 5:
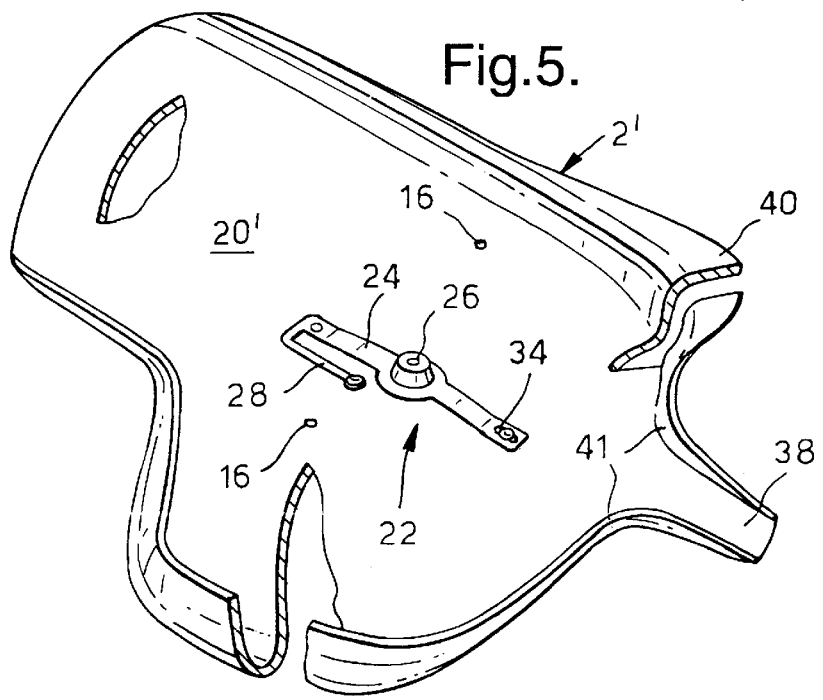

FIG. 5 is the analogue of FIG. 2, also showing terminal element 22.

The electrode positioners according to the present invention are advantageously supplied in sets, in which each of the electrodes is of a different size location and orientation. Experience has shown that, for, e.g., forearm stimulation, trial-and-error selection from a set of seven electrode positioners (four for extensors and three for flexors) will produce satisfactory results for the great majority of patients. However, it should be understood that sets either larger or smaller, or of different proportions of flexor and extensor positioners, are definitely within the scope of the present invention.

Each set also includes a number of surface electrodes 8 and 8' of different sizes, ready for mounting by the clinician, as will be described further below.

Figure 6:
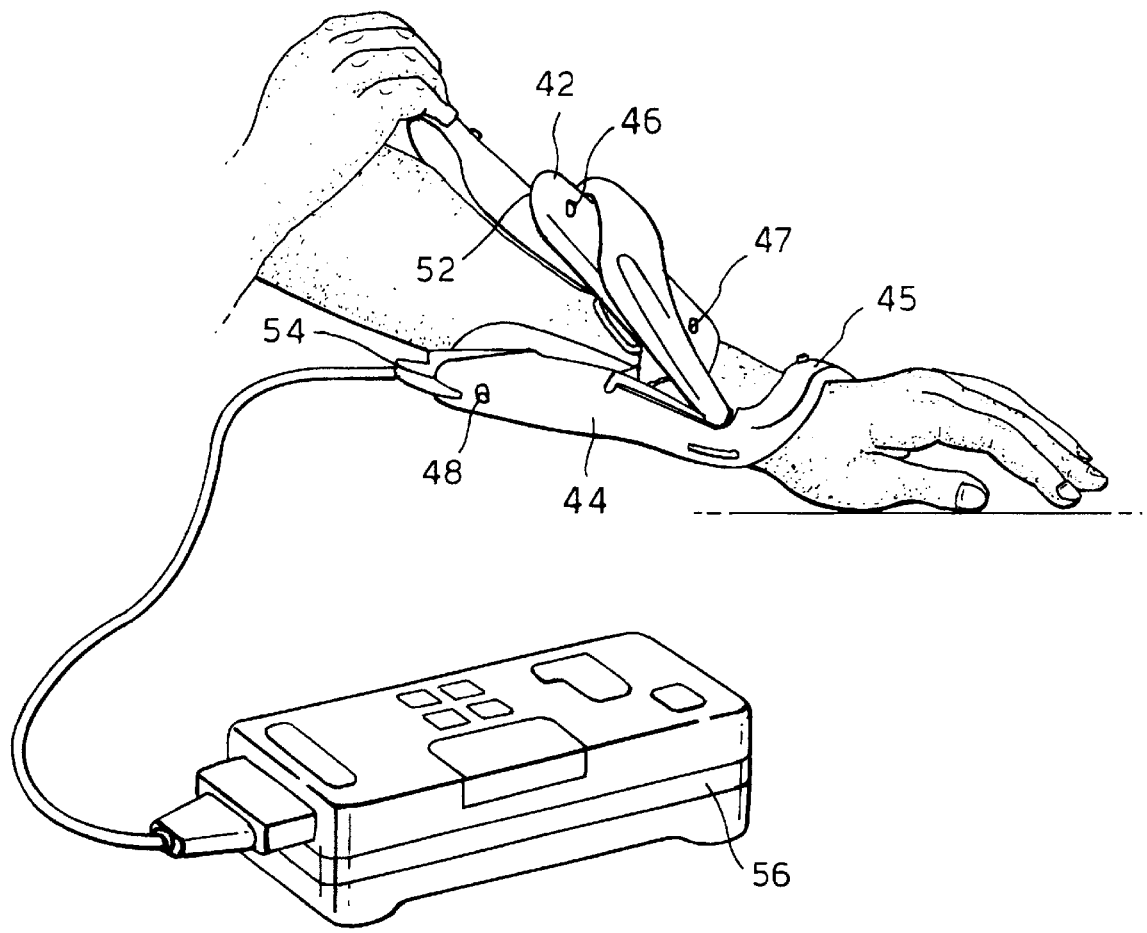

Whether the electrode positioner is selected by the clinician, or, as will be explained, by the patient himself, the positioner must be introduced between the patient's skin and the interior surface of the relevant splint member, as seen in FIG. 6. In either case, two conditions must be met:

1) Upon being fully introduced, the electrode positioner must encounter a definite stop to ensure that its final position relative to the splint is always the same.

2) Efficient contacts for the supply of stimulation current must be ensured.

FIG. 6 shows one way in which these conditions can be fulfilled. Seen is a crocodile-type splint having an upper jaw 42 and a lower jaw 44, with a bow-like member 45 defining and stabilizing the spatial relationship between limb and splint. Further provided in the splint are holes 46, 47 and 48. The distance between, and location of, holes 46 and 47 equals the distance between, and location of, the conical projections 26 of FIG. 2, so that electrode positioner 2 is fully inserted when spring-loaded projections 26 index in holes 46, 47, thereby effectively retaining the positioner. The stimulation current can then be supplied through these holes. With the electrode positioner associated with lower splint jaw 44, the situation is analogous.

An alternative way to define the final position of the electrode positioner with splints lacking holes 46, 47 and 48, is to use edges 52, 54, respectively, of upper and lower jaws 42, 44 as stops against which abuts heel 5 (FIGS. 1, 2) of the extensor electrode positioner, or rims 41 of the flexor electrode positioner (FIG. 5).

Stimulation current can also be supplied by soldering the ends of cables from stimulator 56 into hollow rivets 30 (FIG. 3).

The electrode positioners according to the present invention can be used in two different modes:

1) In the clinic, the clinician fits an as yet electrode-less splint onto the patient's forearm and then, in rapid succession, assesses the response of the limb to the different electrode arrays and combinations of the sets of electrode positioners, selecting the pair of positioners that produces the best results. The clinician then removes the splint and, with the selected positioners still in position, proceeds to indicate the future positions of the permanent surface electrodes to be attached to the splint by using a thin marker and marking dots on the inside surfaces of the respective splint sections through holes 16 (FIGS. 1, 4). The clinician now removes the electrode positioners, selects electrodes of the proper size from the electrode set, peels off the protective silicon paper from the adhesive patch at the back of each electrode, and then mounts each permanent electrode so that its index marks (reference numeral 18 in FIGS. 1 and 4) are in alignment with the dots on the splint sections. Electrical connection is provided by piercing the mounted electrode to transfer the location of the threaded metal terminals mounted in holes 46, 47, 48 of the splint (FIG. 6) and using a screw driven through the pierced electrode to establish permanent contact.

2) In this mode, the clinician does not mount a permanent electrode, but selects a number of electrode positioners for the patient, who, returning home, can now insert his own choice of positioners according to the limb position he desires, which in turn depends on the activity he wishes to carry out, or the exercise program preferred.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is::

1. A set of electrode positioners for skin-contacting surface electrodes used for electrical muscular stimulation in combination with a splint, each said positioner comprising:

at least one electrode positioner in the form of a scoop-like structure, the concave surface of which substantially fits a first surface of a patient's limb;

at least one surface electrode of a predetermined size, location and orientation, fixedly attached to said concave surface, and terminal means for connecting said at least one electrode to a source of stimulation current, said terminal means being accessible from the rear side of said concave surface, wherein said electrode positioner is configured to be introducible between the surface of said limb and an interior surface of said splint, means for arresting said positioner in a predetermined and reproducible final position relative to said splint.

2. The set of electrode positioners as claimed in claim 1, wherein said surface electrode comprises an electrode carrier attachable to the concave surface of said scoop-like structure, a conductive layer connected to said carrier, and a skin-contacting fabric pad connected to said layer.

3. The set of electrode positioners as claimed in claim 2, further comprising a metal terminal located in said splint, wherein said terminal means is a spring-loaded conical metal projection mounted on the rear side of said concave surface and electrically connected to said conductive layer, said projection, in said final position, contacting said metal terminal and connectable to said source of stimulation current.

4. The set of electrode positioners as claimed in claim 3, wherein said terminal means further comprises a metal tongue in conductive connection with said spring-loaded conical projection, said metal tongue being adapted to receive an end of a cable for connecting said surface electrode and said source of stimulation current.

5. The set of electrode positioners as claimed in claim 3, further comprising a recess in said splint, wherein said means for arresting said positioner is constituted by said conical projection, said conical projection defining the final position of said electrode positioner by engagement with said recess in said splint.

6. The set of electrode positioners as claimed in claim 1, wherein said means for arresting said positioner is constituted by a heel member of said scoop-like structure, said heel member defining said final position of said positioner by abutting against an edge of said splint.

7. The set of electrode positioners as claimed in claim 1, further comprising an index mark on each of two edges of said electrode carrier and stencil means in the form of two relatively small holes provided in said scoop-like structure immediately adjacent to said index mark.

8. The set of electrode of positioners as claimed in claim 1, wherein said set comprises a plurality of electrode positioners, the size, location and orientation of the surface electrodes including in said set being preselected so as to cover the requirements of a majority of said patients.

9. The set of electrode positioners as claimed in claim 1, further comprising a selection of surface electrodes of different sizes for attachment to said splint as permanent electrodes.

* * * * *